(12) United States Patent
Cahill-O'Brien

(10) Patent No.: US 9,005,423 B2
(45) Date of Patent: Apr. 14, 2015

(54) PIPELINE COMMUNICATIONS

(71) Applicant: Itron, Inc., Liberty Lake, WA (US)

(72) Inventor: Barry Cahill-O'Brien, Spokane, WA (US)

(73) Assignee: Itron, Inc., Liberty Lake, WA (US)

( * ) Notice: Subject to any disclaimer, the term of this patent is extended or adjusted under 35 U.S.C. 154(b) by 154 days.

(21) Appl. No.: 13/693,497

(22) Filed: Dec. 4, 2012

(65) Prior Publication Data

US 2014/0151241 A1    Jun. 5, 2014

(51) Int. Cl.
*C23F 13/00* (2006.01)
*C23F 13/04* (2006.01)
*C23F 13/22* (2006.01)
*G01N 17/02* (2006.01)

(52) U.S. Cl.
CPC ............... *C23F 13/04* (2013.01); *C23F 13/22* (2013.01); *G01N 17/02* (2013.01); *C23F 2213/32* (2013.01)

(58) Field of Classification Search
CPC ...... C23F 13/04; C23F 13/22; C23F 2213/10; C23F 2213/32; G01N 17/02; G01N 17/04; H04Q 9/00; F16L 2201/30
USPC ............ 204/196.03, 196.04, 196.05, 196.07, 204/196.36, 196.02, 196.1; 205/726, 727, 205/728, 729, 724, 725; 324/700; 340/870.01, 870.09, 870.11, 870.39, 340/870.02
See application file for complete search history.

(56) References Cited

U.S. PATENT DOCUMENTS

| | | | |
|---|---|---|---|
| 1,139,956 A | 5/1915 | Craft |
| 1,958,159 A | 5/1934 | Bresson |
| 2,021,041 A | 11/1935 | Altamura |
| 2,558,188 A | 6/1951 | McWilliams |
| 2,699,177 A | 1/1955 | Wingfield |
| 2,903,540 A | 9/1959 | Gloviak et al. |
| 2,931,876 A | 4/1960 | Weinfurt |
| 3,346,710 A | 10/1967 | Weston et al. |
| 3,378,663 A | 4/1968 | Abramowitz |
| 3,381,105 A | 4/1968 | Mortenson |

(Continued)

FOREIGN PATENT DOCUMENTS

| | | |
|---|---|---|
| CH | 281257 | 2/1952 |
| DE | 619902 | 10/1935 |

(Continued)

OTHER PUBLICATIONS

Capacitors 101 .(Midwest Rural Energy Council, 2006, http://www.mrec.org/Stray_Voltage/Capacitors%20for%20MREC.pdf).*

(Continued)

*Primary Examiner* — Luan Van
*Assistant Examiner* — Alexander W Keeling
(74) *Attorney, Agent, or Firm* — Dority & Manning, P.A.

(57) ABSTRACT

Communications systems are provided for use with an impressed current cathodic protection (ICCP) system having single or multiple ICCP components. A pipeline may be provided by connecting multiple pipeline sections together as an integrated pipeline where each section has an associated ICCP system. A communications signal comprising an AC signal is impressed on the pipeline and received by receivers associated with power supplies associated with each ICCP system. Upon reception of the AC signal, a controllable switch is operated within the power supplies to synchronously disconnect them from their power source and thereby enable accurate testing of the ICCP system.

7 Claims, 1 Drawing Sheet

(56) References Cited

U.S. PATENT DOCUMENTS

| | | | |
|---|---|---|---|
| 3,632,935 A | 1/1972 | Stegmaier | |
| 3,689,856 A | 9/1972 | Lambert et al. | |
| 3,751,618 A | 8/1973 | Hallerberg | |
| 3,842,228 A | 10/1974 | Green | |
| 3,902,032 A | 8/1975 | Koepke | |
| 4,006,323 A | 2/1977 | Nelson et al. | |
| 4,087,669 A | 5/1978 | Sauer | |
| 4,178,572 A | 12/1979 | Gaskill et al. | |
| 4,230,388 A | 10/1980 | Thierry et al. | |
| 4,240,030 A | 12/1980 | Bateman et al. | |
| 4,309,581 A | 1/1982 | Macaire et al. | |
| 4,321,436 A | 3/1982 | McGarrity | |
| 4,357,509 A | 11/1982 | Adlerteg | |
| 4,412,116 A | 10/1983 | Golub | |
| 4,490,593 A | 12/1984 | Cook | |
| 4,550,232 A | 10/1985 | Lemmer | |
| 4,562,323 A | 12/1985 | Belbel et al. | |
| 4,597,619 A | 7/1986 | Reimer | |
| 4,621,303 A | 11/1986 | Rowe | |
| 4,658,365 A * | 4/1987 | Syrett et al. | 205/724 |
| 4,801,772 A | 1/1989 | Bratkowski et al. | |
| 4,826,577 A * | 5/1989 | Lange | 205/734 |
| 4,866,633 A | 9/1989 | Nakane et al. | |
| 5,021,760 A | 6/1991 | Krubsack et al. | |
| 5,040,599 A * | 8/1991 | Pfalser et al. | 166/248 |
| 5,045,969 A | 9/1991 | Menasco | |
| 5,227,750 A | 7/1993 | Connell et al. | |
| 5,296,660 A | 3/1994 | Morel et al. | |
| 5,296,662 A | 3/1994 | Engdahl et al. | |
| 5,546,269 A | 8/1996 | Robinson et al. | |
| 5,572,396 A | 11/1996 | Robinson | |
| 5,575,309 A | 11/1996 | Connell | |
| 5,583,471 A | 12/1996 | Weiser et al. | |
| 5,586,913 A | 12/1996 | Robinson et al. | |
| 5,608,598 A | 3/1997 | Dieppedalle et al. | |
| 5,668,538 A | 9/1997 | Warwick | |
| 5,694,099 A | 12/1997 | Connell et al. | |
| 5,748,104 A | 5/1998 | Argyroudis et al. | |
| 5,801,643 A | 9/1998 | Williams et al. | |
| 5,821,481 A | 10/1998 | Neubauer | |
| 5,853,305 A | 12/1998 | Bedrossian et al. | |
| 5,886,860 A | 3/1999 | Chen et al. | |
| 5,952,739 A | 9/1999 | Grass et al. | |
| 6,000,931 A | 12/1999 | Tanabe et al. | |
| 6,034,585 A | 3/2000 | Donhauser | |
| 6,046,660 A | 4/2000 | Gruner | |
| 6,046,661 A | 4/2000 | Reger et al. | |
| 6,056,008 A | 5/2000 | Adams et al. | |
| 6,080,949 A | 6/2000 | Weber et al. | |
| 6,088,659 A | 7/2000 | Kelley et al. | |
| 6,104,586 A | 8/2000 | Robinson | |
| 6,246,306 B1 | 6/2001 | Gruner | |
| 6,252,478 B1 | 6/2001 | Gruner | |
| 6,292,075 B1 | 9/2001 | Connell et al. | |
| 6,320,485 B1 | 11/2001 | Gruner | |
| 6,366,217 B1 | 4/2002 | Cunningham et al. | |
| 6,437,692 B1 | 8/2002 | Petite et al. | |
| 6,441,332 B1 | 8/2002 | Crawford et al. | |
| 6,470,903 B2 | 10/2002 | Reyman | |
| 6,513,545 B2 | 2/2003 | Rhone et al. | |
| 6,520,798 B1 | 2/2003 | Robinson et al. | |
| 6,563,409 B2 | 5/2003 | Gruner | |
| 6,625,570 B2 * | 9/2003 | Pierro et al. | 702/188 |
| 6,661,319 B2 | 12/2003 | Schmelz | |
| 6,788,176 B2 | 9/2004 | Schmelz | |
| 6,892,751 B2 | 5/2005 | Sanders | |
| 6,906,637 B2 | 6/2005 | Martin | |
| 6,994,309 B2 | 2/2006 | Fernandez-Sein | |
| 7,027,957 B2 | 4/2006 | Fourie et al. | |
| 7,049,932 B2 | 5/2006 | French et al. | |
| 7,058,523 B2 | 6/2006 | Ramirez | |
| 7,064,671 B2 | 6/2006 | Vanderah et al. | |
| 7,068,052 B2 | 6/2006 | Hilleary et al. | |
| 7,069,161 B2 | 6/2006 | Gristina et al. | |
| 7,088,239 B2 | 8/2006 | Basinger et al. | |
| 7,130,722 B2 | 10/2006 | Soni | |
| 7,265,652 B2 | 9/2007 | Ying | |
| 7,271,987 B1 | 9/2007 | Zhang et al. | |
| 7,298,288 B2 | 11/2007 | Nagy et al. | |
| 7,362,232 B2 | 4/2008 | Holle et al. | |
| 7,458,387 B2 | 12/2008 | McGill | |
| 7,458,846 B2 | 12/2008 | Loehr et al. | |
| 7,833,034 B2 | 11/2010 | Connell | |
| 8,133,381 B2 * | 3/2012 | Ersoy | 205/740 |
| 8,228,078 B2 | 7/2012 | Herraez et al. | |
| 8,310,251 B2 * | 11/2012 | Orazem | 324/713 |
| 2001/0010032 A1 | 7/2001 | Ehlers et al. | |
| 2002/0030604 A1 | 3/2002 | Chance et al. | |
| 2002/0039069 A1 | 4/2002 | Chance et al. | |
| 2002/0050885 A1 | 5/2002 | Gruner | |
| 2005/0162149 A1 | 7/2005 | Makinson et al. | |
| 2005/0174256 A1 | 8/2005 | Berg | |
| 2006/0031180 A1 | 2/2006 | Tamarkin et al. | |
| 2006/0066425 A1 | 3/2006 | Gruner | |
| 2006/0278269 A1 | 12/2006 | McGill | |
| 2007/0035315 A1 * | 2/2007 | Hilleary | 324/700 |
| 2007/0211768 A1 | 9/2007 | Cornwall et al. | |
| 2008/0177678 A1 | 7/2008 | Di Martini et al. | |
| 2008/0290986 A1 | 11/2008 | Laughlin-Parker et al. | |
| 2010/0036939 A1 | 2/2010 | Yang et al. | |
| 2011/0000310 A1 | 1/2011 | Yokohata et al. | |
| 2011/0074598 A1 | 3/2011 | Cornwall et al. | |
| 2011/0074600 A1 | 3/2011 | Cornwall et al. | |
| 2011/0074601 A1 | 3/2011 | Cornwall | |
| 2011/0074602 A1 | 3/2011 | Cornwall et al. | |
| 2011/0074603 A1 | 3/2011 | Cornwall et al. | |
| 2011/0078063 A1 | 3/2011 | Cahill-O'Brien et al. | |
| 2011/0078093 A1 | 3/2011 | Johnson et al. | |
| 2011/0273305 A1 | 11/2011 | Osterloh et al. | |
| 2013/0292263 A1 * | 11/2013 | Carr | 205/726 |

FOREIGN PATENT DOCUMENTS

| | | |
|---|---|---|
| DE | 1753688 | 10/1957 |
| EP | 0 241 440 A2 | 10/1987 |
| EP | 0532586 | 4/1996 |
| EP | 0714549 | 5/1998 |
| EP | 0643813 | 6/1998 |
| EP | 1 152 235 A1 | 11/2001 |
| GB | 1384294 | 2/1975 |
| GB | 2 317 797 A | 4/1998 |
| WO | WO 88/08462 A1 | 11/1988 |
| WO | WO 91/19314 | 12/1991 |
| WO | WO 94/23230 | 10/1994 |
| WO | WO 95/05671 | 2/1995 |
| WO | WO/98/40898 | 9/1998 |
| WO | WO 03/046936 | 6/2003 |
| WO | WO 03/049129 | 6/2003 |
| WO | WO 2005/106907 | 11/2005 |
| WO | WO 2006/024855 | 3/2006 |
| WO | WO 2006/035235 | 4/2006 |
| WO | WO 2009/110192 | 9/2009 |

OTHER PUBLICATIONS

PCT International Search Report for PCT International Application No. PCT/US2013/056111 completed Jan. 24, 2014, mailed Feb. 4, 2014.

PCT Written Opinion of the International Searching Authority for PCT International Application No. PCT/US2013/056111, completed Jan. 24, 2014, mailed Feb. 4, 2014.

Machine translation of DE 619902 listed above, Jan. 27, 2011.

Machine translation of CH 281257 listed above, Jan. 27, 2011.

BLP, "X-Pulse: Introducing The New Residential Total Disconnect/Reconnect System", Power & Utilities brochure.

Thomas E. Browne, Jr., Editor; "Circuit Interruption Theory and Techniques", Westinghouse Research and Development Center, Pittsburgh, Pennsylvania, Copyright 1984 by Marcel Dekker, Inc.

Slade, *Electric Contact Phenomena*, pp. 586-593.

David J. Southern P.E., Product Development Manager, FreeWave Technologies, Inc., "Operators Extend SCADA Investment to Vital Cathodic Protection", pp. 16-17 of *Remote Site & Equipment Management Magazine*, Jun./Jul. 2008.

(56) References Cited

OTHER PUBLICATIONS

PCT International Search Report for PCT International Application No. PCT/JP2009/000816 mailed Apr. 28, 2009.

PCT International Search Report for PCT International Application No. PCT/US2009/045555 mailed Jul. 20, 2009.

International Search Report for PCT International Application No. PCT/US2009/045554 Mailed Jul. 29, 2009.

PCT International Search Report for PCT International Application No. PCT/US2010/049820 dated Nov. 15, 2010.

PCT Written Opinion of the International Searching Authority for PCT International Application No. PCT/US2010/049820 dated Nov. 15, 2010.

PCT International Search Report for PCT International Application No. PCT/US2010/050383 dated Nov. 18, 2010.

PCT Written Opinion of the International Searching Authority for PCT International Application No. PCT/US2010/050383 dated Nov. 18, 2010.

PCT International Search Report for PCT International Application No. PCT/US2010/050340 dated Nov. 26, 2010.

PCT Written Opinion of the International Searching Authority for PCT International Application No. PCT/US2010/050340 dated Nov. 26, 2010.

USPTO Non-Final Office Action issued Dec. 1, 2011 for U.S. Appl. No. 12/890,786.

* cited by examiner

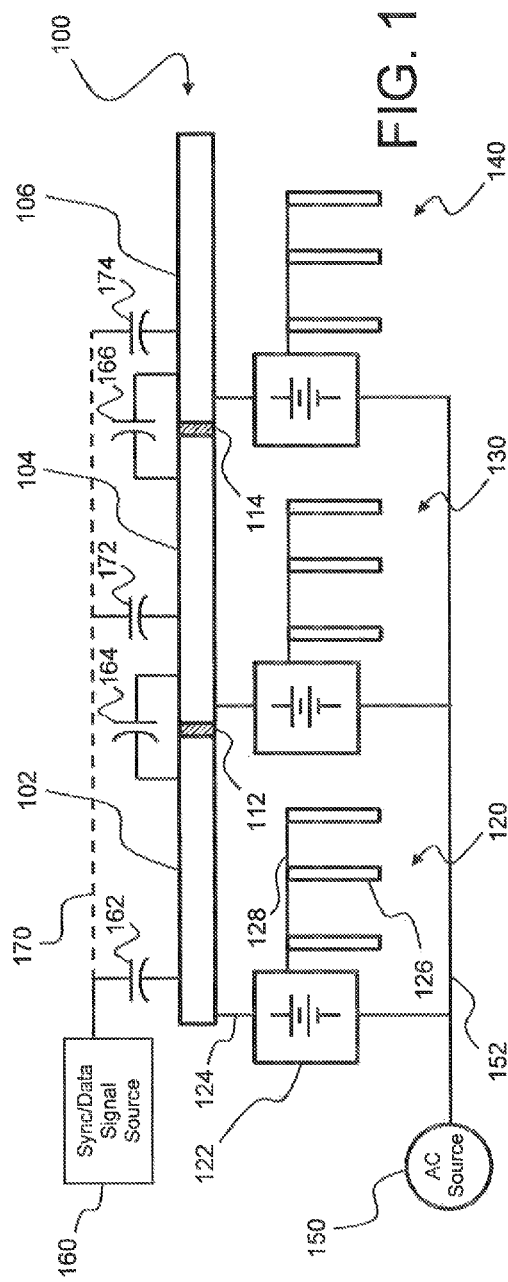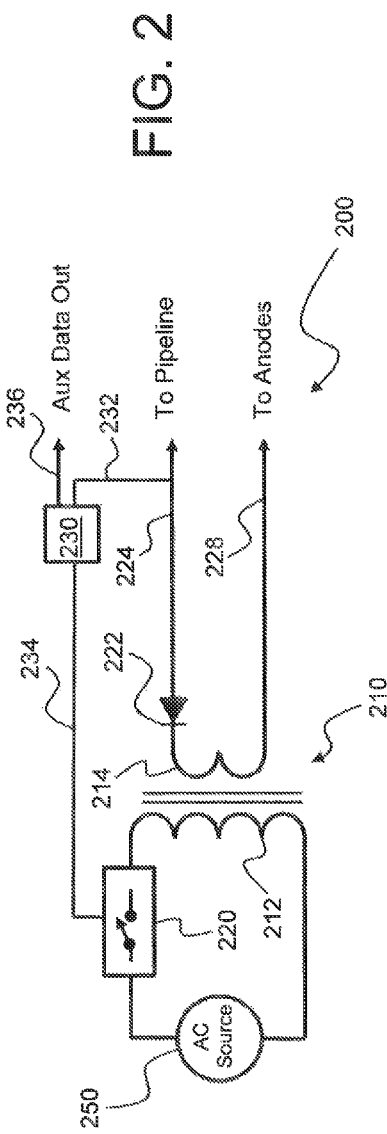

PIPELINE COMMUNICATIONS

FIELD OF THE SUBJECT MATTER

The presently disclosed subject matter relates to communications systems. More particularly, the presently disclosed subject matter relates to associated methods and apparatus for permitting nodes on a cathodically protected pipeline to communicate and to synchronize operations, using the pipe as a communications medium.

BACKGROUND OF THE SUBJECT MATTER

Buried pipelines are commonly provided with systems to protect them from corrosion. Such protection systems generally include some form of cathodic protection. In such system, it is a general requirement to monitor the protection on a periodic basis to ensure sufficient protection is applied to prevent corrosion.

Generally there are two forms of cathodic protection in use today on pipelines. They include galvanic protection systems and impressed current systems. In galvanic systems, a sacrificial anode is used as the source of an electrical potential, which protects the pipeline. Galvanic protection systems are generally used primarily for short segments of pipe and in relatively conductive soils. In such systems, the segments of pipe are electrically isolated from each other and implementation of monitoring stations is relatively easy due to the low potential voltages, and small electrical currents. As the amount of pipeline increases and/or the conductivity of the soil decreases, a simple galvanic anode no longer suffices to provide protection.

As further understood by those of ordinary skill in the art, the sacrificial anodes (galvanic systems) are their own source, because as they dissolve they generate current. In other words, sacrificial anodes have very limited current capability but do not need a power source. Stated another way, sacrificial anodes are often used in short segments of pipe, while non-sacrificial anodes with ICCP (impressed current cathodic protection) are used to cover relatively longer segments of pipe which are too large to be covered by sacrificial anodes. In such instances, as understood by those of ordinary skill in the art, a DC supply is used between a pipe and a non-sacrificial anode since it cannot itself normally generate current.

Therefore, in instances where galvanic protection is inadequate, protections systems employing one or more transformer and rectifier systems are used to impress a protective electrical current on the pipeline. A number of transformers may be used and distributed along the pipeline to provide significant current to provide appropriate levels of protection. Because such systems are active, and protects significant amounts of pipe, a more rigorous monitoring system is required. At present, the industry standard practice for providing such monitoring frequently requires turning off the transformer for a short amount of time, typically for such as one second, to get an accurate measurement of the protection potential. This is due to the possible inaccuracies caused by interference between the monitoring system, and the current flow from the transformer injecting the protection current.

In addition, if there are numerous transformers, they need to be turned off synchronously to measure the protection. It would be advantageous, therefore, to provide a communications system to insure proper synchronization of the numerous transformers within a pipeline protection system during such measurement periods.

While various implementations of cathodic protection systems have been developed, and while various combinations of control systems have been developed, no design has emerged that generally encompasses all of the desired characteristics as hereafter presented in accordance with the subject technology.

SUMMARY OF THE SUBJECT MATTER

In view of the recognized features encountered in the prior art and addressed by the presently disclosed subject matter, improved methodology and associated apparatus for synchronizing operation of a plurality of transformers in an impressed current cathodic protection system have been provided.

The presently disclosed subject matter relates in pertinent part to methodology for synchronizing power control switching of single or multiple individual ICCP systems associated with a pipeline. In accordance with such exemplary method, an alternating current (AC) signal is impressed on at least selected ones of respective sections of such pipeline and individual ICCP systems are disabled in accordance with characteristics of a received impressed AC signal. In selected embodiments, individual ICCP system power supplies may be disabled by disconnecting their transformers from their normal power source. In selected embodiments, presently disclosed exemplary methodology may employ a controllable switch to disconnect the transformers.

Presently disclosed methodology, in selected embodiments, may provide for impressing a communications signal comprising an alternating current (AC) signal corresponding to a low voltage AC signal on at least selected ones of the multiple sections that, in some embodiments, may correspond to an AC signal which has a potential level up to a certain relatively low voltage level, such as about 15 volts AC. In some embodiments, presently disclosed methodology may provide for capacitive coupling the AC signal to the multiple sections.

The presently disclosed subject matter also relates in pertinent part to an associated impressed current cathodic protection (ICCP) system. Such systems may comprise a pipeline that is separated into multiple direct current (DC) isolated pipeline sections and a plurality of power supplies, individual ones of which are associated with individual ones of the pipeline sections, and each of which may respectively include a controllable switch configured to disconnect the power supply from a source of AC power. In such system, each of the power supplies include an associated receiver configured to listen for a signal from an alternating current (AC) signal source coupled to at least selected of the pipeline sections. Upon hearing an AC signal, the receivers can cause the controllable switch to disconnect the power supply from its source of AC power. In selected embodiments, each of the plurality of power supplies includes a transformer that is disconnected from the AC power source by operation of its associated controllable switch.

In certain presently disclosed embodiments, an exemplary system may further include one or more anode elements associated with each of the pipeline sections and with each of the plurality of power supplies configured to supply a direct current (DC) voltage between its associated pipeline section and the one or more of the anode elements associated with its associated pipeline section. In selected embodiments, the power supplies may be configured to supply a specific range of currents at about a designated voltage, such as from about 10 to about 50 amperes of current at about 50 volts DC.

In accordance with other features of some embodiments of the presently disclosed system subject matter, the AC signal source may be capacitively coupled to at least selected of the multiple isolated pipeline sections, while in some embodiments, the pipeline sections are capacitively coupled together. In particular embodiments, the AC signal source may comprise an AC source of a relatively low voltage, such as about 15 volts AC or less.

Additional embodiments of the presently disclosed subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments and uses of the subject matter without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the presently disclosed subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the presently disclosed subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the presently disclosed subject matter, including the best mode thereof, directed to one of ordinary skill in the art, is set forth in the specification, which makes reference to the appended figures, and reflecting both presently disclosed methodology and apparatus, in which:

FIG. 1 illustrates an exemplary portion of a pipeline incorporating aspects of the presently disclosed subject matter; and FIG. 2 illustrates an exemplary block diagram of a power supply and control system constructed in accordance with the presently disclosed subject matter.

Repeat use of reference characters throughout the present specification and appended drawings is intended to represent same or analogous features, elements, or steps.

DETAILED DESCRIPTION OF THE SUBJECT MATTER

As discussed in the Summary of the Subject Matter section, the presently disclosed subject matter is particularly concerned with associated methods and apparatus for permitting nodes on a cathodically protected pipeline to communicate and to synchronize operations.

Selected combinations of aspects of the presently disclosed technology correspond to a plurality of different embodiments of the presently disclosed subject matter. It should be noted that each of the exemplary embodiments presented and discussed herein should not insinuate limitations of the presently disclosed subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

The presently disclosed subject matter takes advantage of the physical presence of a pipeline to provide a communications medium to synchronize cathodic protection transformers and measurement systems, to precisely the same time, to allow a synchronous turn off of the cathodic protection system, and to allow accurate measurements to be made.

There are a number of standard measurements presently employed to test pipeline cathodic protection systems. These tests include such as "instant off," and polarization decay measurements which must be made within milliseconds of turning off the power to the transformer. Such tests are well known to those of ordinary skill in the art and will not be further described here. In conducting such well known tests (details of which form no particular part of the presently disclosed subject matter), power to the cathodic protection system cannot be left off for very long as the protection barrier created by the potential voltage can decay rapidly. In view of such known rapid decay, the usage of outages on the order of one second are typical.

In a cathodic protection system where measurements are made on an infrequent basis, for example, daily or monthly, it is clear that an accurate synchronization method is needed. Traditional systems require the use of precise timing devices to synchronize the system, such as GPS time clocks, radio modems, etc. In accordance with the presently disclosed subject matter, a signaling system is provided wherein the timing data is sent when needed by way of an alternating current (AC) signal imposed upon the pipeline itself. Also not separately illustrated, it will be understood from the illustration of FIG. 1 that isolators (for example, 112 and 114) may be eliminated, in which case FIG. 1 also represents the use of multiple ICCP stations on a common section or segment of a pipeline. Subsequently, the isolators can be included when considering the perspective of communications along the pipeline from various groups of ICCP stations to a control center or collection point. It is intended that all such subject matter is represented by the illustration of FIG. 1.

Reference will now be made in detail to exemplary presently preferred embodiments of the subject pipeline communications system, with the subject figures disclosing both apparatus and associated methodology. With reference to FIG. 1, there is illustrated an exemplary portion of a pipeline 100 incorporating aspects of the presently disclosed subject matter. As seen in FIG. 1, an exemplary three respective pipeline portions (sections) 102, 104, 106 are coupled together by way of electrically isolating coupling device 112, 114 that are configured to block the flow of any direct current between the pipeline portions. Those of ordinary skill in the art will appreciate that the three illustrated portions are exemplary and that an actual pipeline may incorporate many more similar portions. The pipeline portions 102, 104, and 106 are each provided with their own separately operable cathodic protection systems 120, 130, 140. Each of the cathodic protections systems may be configured to receive power from AC source 150 or from other AC sources, not separately illustrated.

In an exemplary configuration, pipelines may be routinely protected such as by a coating supplemented with cathodic protection. An Impressed Current Cathodic Protection (ICCP) system for such a protected pipeline configuration would generally include a DC power source, which as generally known may be often an AC powered rectifier and an anode, or array of anodes buried in the ground. The DC power source may typically have a DC output of between about 10 and about 50 amperes and about 50 volts, but as well known such specifics may depend on several factors, such as the size of the pipeline, location, and soil resistivity. The output of the DC source would then be adjusted to the optimum level after conducting various tests including measurements of electro-chemical potential, all as well known to those of ordinary skill in the art, and the details of which form no particular part of the presently disclosed subject matter.

With further reference to FIG. 1, representative cathodic protection system 120 includes a direct current (DC) power supply 122 having a negative output terminal coupled to pipeline portion 102 by way of line 124 and a positive output terminal coupled to one or more anode elements, representatively anode 126, by way of line 128. As noted above, the anodes in this case are not sacrificial as the rectifier provides the current, and not the electro-chemical action of the anode dissolving into the soil. The anodes in this case are typically a specialized material such as carbon rods or mu-metal anodes (as understood, mu-metal generally refers to a range of nickel-iron alloys that are notable for their high magnetic permeability). In accordance with the presently disclosed subject matter, power supply 122 associated with pipeline section 102 (along with equivalent power supplies associated with all remaining pipeline sections) may be controlled by way of a signal source 160 as is more fully explained herein with respect to FIG. 2. As previously noted, it is desirable to be able to synchronize operations of the various cathodic protection system power supplies for measurement purposes.

In accordance with the presently disclosed subject matter, signal source 160 is configured to supply a relatively low level AC signal to each section 102, 104, and 106 of the pipeline 100. Such AC signals may be coupled in any suitable manner to the pipeline sections 102, 104, 106, for example by way of coupling capacitors 162, 164, 166 where capacitors 164 and 166 may be configured to bridge electrically isolating coupling devices 112, 114 to pass an AC signal while continuing to inhibit passage of a DC cathodic protection voltage from one pipeline section to another. In an alternative embodiment, a single signal line 170 (shown in dotted line in FIG. 1) from signal source 160 may be coupled by way of individual capacitors 162, 172, 174 to respective pipeline sections 102, 104, 106. In either exemplary embodiments, a relatively low AC voltage (such as of up to about 15 Volts AC) may be preferably employed as the signaling voltage and still be considered non detrimental to the cathodic protection system.

In accordance with the presently disclosed subject matter (apparatus and associated methodology), all power supplies are preferably configured to listen for such relatively low AC signal and can thereby be easily synchronized such that multiple transformers can be turned off while accurate measurements are made. Such measurements may be made at multiple points along the segment or section (portion) of pipeline at locations which will be well understood by those of ordinary skill in the art, without further detailed description thereof. Data collected by such test stations may per presently disclosed subject matter be communicated over the pipeline to a collection point such as a central monitoring station, or read directly with another communications method. In certain instances where communications are over or along the pipeline, the low voltage AC signal may comprise a modulated signal for providing communications data (such as measurement data on protection potential) along such pipeline to a collection point. Such presently disclosed functionality enables measurements to be non-continuous or only as required, enabling the test instruments to be battery powered. In addition, measurements on galvanic sections of pipeline could be triggered and reported using a similar signaling approach, as will be understood by those of ordinary skill in the art.

Referring to FIG. 2 there is illustrated an exemplary block diagram of a representative power supply and control system generally 200 constructed in accordance with the presently disclosed subject matter. Individual power supplies and control systems 200 are employed for each of the power supplies 122, 124, 126 of FIG. 1. Each power supply and control system 200 includes a transformer 210 coupled such as by way of an exemplary primary winding 212 and a controllable switch 220 to a representative AC source 250. Exemplary output winding 214 of transformer 210 is preferably then coupled by way of a representative rectifier 222 to an associated pipeline section by way of line 224 and to associated anodes (not separately illustrated) by way of line 228.

In accordance with the presently disclosed subject matter, a signal receiver 230 is incorporated with the power supply and is configured to monitor signals impressed on pipeline 100 by way of line 232. In one embodiment of the presently disclosed subject matter, such monitored signals may then be used to synchronize operation of control switches such as controllable switch 220 coupled in series between AC source 250 and transformer 210 primary winding 212. Operation of such controllable switch based on instructions from receiver 230 functions to remove power to the various cathodic protection systems to permit testing of the system. Those of ordinary skill in the art are well familiar with the general scope of such testing traditionally involved with the ongoing testing requirements for cathodic protection systems. As the particular aspects of such testing form no part of the present disclosure except for the ability to synchronize disconnection of the various transformers, such known measurement devices and procedures have not been separately illustrated to better simplify the subject drawings and because such are not necessary to fully illustrate the presently disclosed subject matter.

In accordance with a further aspect of the presently disclosed subject matter, aspects of the presently disclosed subject matter may also be employed to include the transmission of data to and/or from various test points along the associated pipeline. In such regard, an auxiliary data signal output may be derived from receiver 230 based on information modulated in any suitable manner on the AC signal sent from source 160 and sent from receiver (transceiver) 230 to output line 236 for any suitable purpose. Similarly, although not separately illustrated herein, additional AC signal sources may be incorporated into the various power supply and control systems 200 and configured to apply a modulated signal to associated pipeline 100 for transmission back to a remote receiver. Such transmissions may include data from any testing measurements taken at the various transformers or any other data as should be desired by the users and/or operators of the subject system. Yet other methods of data collection may be practiced, such as involving wireless RF or logging recorders, in which instances only a synchronization signal is needed.

While the presently disclosed subject matter has been described in detail with respect to specific exemplary embodiments thereof, it will be appreciated that those skilled in the art, upon attaining an understanding of the foregoing, may readily produce alterations to, variations of, and equivalents to such embodiments. Accordingly, the scope of the present disclosure is by way of example rather than by way of limitation, and the subject disclosure does not preclude inclusion of such modifications, variations, and/or additions to the presently disclosed subject matter as would be readily apparent to one of ordinary skill in the art.

What is claimed is:

1. In a pipeline impressed current cathodic protection (ICCP) system, a method of synchronizing power control switching of individual ICCP systems associated with respective sections of such pipeline, comprising:
    impressing an alternating current (AC) signal on at least selected ones of the multiple sections; and
    disabling individual ICCP systems in accordance with characteristics of a received impressed AC signal;
    wherein disabling comprises synchronously disconnecting individual ICCP system power supply transformers from their normal power source.

2. A method as in claim 1, wherein disabling comprises operating a controllable switch.

3. A method as in claim 1, wherein impressing an alternating current (AC) signal comprises impressing a low voltage AC signal on at least selected ones of the pipeline sections.

4. A method as in claim 3, wherein the low voltage AC signal has a potential level up to about 15 volts AC.

5. A method as in claim 3, wherein the low voltage AC signal comprises a modulated signal for providing communications data along the pipeline to a collection point.

6. A method as in claim 3, wherein the low voltage AC signal is impressed on at least selected ones of the multiple sections by way of capacitive coupling of the AC signal to the pipeline sections.

7. A method as in claim 6, wherein the pipeline sections are capacitively coupled together.

* * * * *